United States Patent
Wiesen

(10) Patent No.: US 10,258,725 B2
(45) Date of Patent: Apr. 16, 2019

(54) DEVICE FOR CARRYING OUT A METHOD FOR CONSERVING A BLOOD TREATMENT DEVICE, AND METHOD FOR CONSERVING A BLOOD TREATMENT DEVICE

(71) Applicant: Fresenius Medical Care Deutschland GmbH, Bad Homburg v.d.H. (DE)

(72) Inventor: Gerhard Wiesen, Bad Homburg v.d.H. (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 557 days.

(21) Appl. No.: 13/873,369

(22) Filed: Apr. 30, 2013

(65) Prior Publication Data

US 2013/0284671 A1    Oct. 31, 2013

Related U.S. Application Data

(60) Provisional application No. 61/640,037, filed on Apr. 30, 2012.

(30) Foreign Application Priority Data

Apr. 30, 2012    (DE) .......................... 10 2012 008 551

(51) Int. Cl.
    *A61M 1/16*    (2006.01)
    *A61M 1/34*    (2006.01)

(52) U.S. Cl.
    CPC .............. *A61M 1/16* (2013.01); *A61M 1/168* (2013.01); *A61M 1/1682* (2014.02); *A61M 1/3465* (2014.02)

(58) Field of Classification Search
    CPC ....... A61M 1/16; A61M 1/168; A61M 1/3465

(Continued)

(56) References Cited

U.S. PATENT DOCUMENTS

4,493,693 A * 1/1985 Bilstad ................ A61M 1/3496
    600/573
5,641,144 A * 6/1997 Hendrickson ........... A61M 1/16
    128/DIG. 26

(Continued)

FOREIGN PATENT DOCUMENTS

DE    196 05 260    11/1996
FR    2 700 121 A1    7/1994

OTHER PUBLICATIONS

International Preliminary Report on Patentability, dated Nov. 4, 2014, from corresponding International Application No. PCT/EP2013/001265.

(Continued)

*Primary Examiner* — Krishnan S Menon
*Assistant Examiner* — Brad Gordon
(74) *Attorney, Agent, or Firm* — Kilyk & Bowersox, P.L.L.C.

(57) ABSTRACT

The present invention relates to extracorporeal blood treatment devices and methods and devices for conserving extracorporeal blood treatment devices. In accordance with the present invention, an antifreeze agent in introduced only into that part of the dialysis liquid system of the blood treatment device that includes the volume lying upstream of a sterile filter with which sterile substituate is recovered from the dialysis liquid. Accordingly, that part of the dialysis liquid system that includes the volume lying downstream of the sterile filter is not filled with an antifreeze agent. The present invention makes it possible, after removal of the sterile filter, to easily and safely separate a substituate segment from the rest of the dialysis liquid system and drain off liquid located in the substituate segment.

18 Claims, 3 Drawing Sheets

(58) Field of Classification Search
USPC .............................. 210/321.6, 541, 636, 646
See application file for complete search history.

(56) References Cited

U.S. PATENT DOCUMENTS

| | | | |
|---|---|---|---|
| 5,863,421 A | | 1/1999 | Peter et al. |
| 5,895,578 A | | 4/1999 | Simard et al. |
| 6,187,207 B1 | * | 2/2001 | Brauer .......................... 210/739 |
| 2004/0222139 A1 | | 11/2004 | Brugger et al. |
| 2005/0065459 A1 | * | 3/2005 | Zhang ................... A61M 1/342 |
| | | | 604/4.01 |
| 2009/0076433 A1 | | 3/2009 | Folden et al. |

OTHER PUBLICATIONS

International Search Report, dated Aug. 21, 2013, from corresponding International Application No. PCT/EP2013/001265.

* cited by examiner

DEVICE FOR CARRYING OUT A METHOD FOR CONSERVING A BLOOD TREATMENT DEVICE, AND METHOD FOR CONSERVING A BLOOD TREATMENT DEVICE

CROSS REFERENCE TO RELATED APPLICATIONS

This application claims the benefit of U.S. Provisional Patent Application No. 61/640,037, filed on Apr. 30, 2012, and German Patent Application No. 10 2012 008 551.6, filed on Apr. 30, 2012.

FIELD OF INVENTION

The present invention relates to a device for carrying out a method for conserving an extracorporeal blood treatment device, and to a method for conserving an extracorporeal blood treatment device. The present invention further relates to an extracorporeal blood treatment device with a device for carrying out a method for conserving the blood treatment device.

BACKGROUND OF INVENTION

The known dialysis devices have an extracorporeal blood circuit and a dialysis liquid system. The dialysis liquid system of the known dialysis devices comprises a dialysis liquid delivery line, which leads from a dialysis liquid source to the dialysis liquid chamber of a dialyser, and a dialysis liquid removal line, which leads from the dialysis liquid chamber of the dialyser to an outflow. While the dialysis liquid flows through the dialysis liquid chamber of the dialyser, substance transport takes place across the membrane of the dialyser into the blood chamber. In what is called hemo(dia)filtration, some of the liquid drawn off through the membrane of the dialyser is replaced by a sterile replacement liquid (substitute), which is delivered to the extracorporeal blood circuit either upstream or downstream of the dialyser. The delivery of the substitute takes place via a substituate line, which leads to the extracorporeal blood circuit.

It has been found in practice that the substituate can be recovered in a sterile state from the dialysis liquid online during the blood treatment.

Dialysis devices are known in which the substituate is recovered from the dialysis liquid during the dialysis treatment (online). In order to ensure that the substituate recovered online is sterile and free of pyrogens, the dialysis liquid is passed through a sterile filter, which is divided into two chambers by a membrane that holds back microorganisms. A dialysis device with a sterile filter for recovering substituate is known from U.S. Pat. No. 6,187,207 B1, for example.

Various methods are known for cleaning and disinfecting blood treatment devices. Before it is put into operation, the blood treatment device is flushed with a liquid that contains a cleaning agent and/or disinfectant. In this way, it is also possible for stubborn contaminants, for example biofilm, algae, protein deposits and blood residues, to be removed safely and quickly.

An exception is when a blood treatment device is kept in storage over quite a long period, particularly before being put into operation for the first time. During this period, there is not only the problem of eliminating the possibility of contamination, but also that of protecting the blood treatment device against freezing. Therefore, for conservation, the liquid systems of the known blood treatment devices are generally filled with an antifreeze agent.

An object of the present invention is to make available a method permitting conservation of an extracorporeal blood treatment device without the danger of formation of contaminants that could not be removed safely and quickly using the known cleaning and disinfecting agents.

It is also an object of the present invention to make available a device with which the method for conserving the blood treatment device can be carried out easily and safely.

A further object of the present invention is to create a blood treatment device with a device for carrying out the conservation method.

Various investigations by the inventor into the causes of bacterial contamination in dialysis liquid systems have shown that the danger of contamination may increase if the dialysis liquid system were to be filled with an antifreeze agent for conserving the blood treatment device.

A method according to the present invention for conserving a blood treatment device reduces the danger of contamination if the dialysis liquid system of the extracorporeal blood treatment device were to be filled with an antifreeze agent. It is based on introducing an antifreeze agent only into that part of the dialysis liquid system that includes the volume lying upstream of the sterile filter with which sterile substituate is recovered from the dialysis liquid. Accordingly, that part of the dialysis liquid system that included the volume lying downstream of the sterile filter is not filled with an antifreeze agent. This part of the dialysis liquid system is referred to hereinbelow as the substituate segment. The two volumes, which are filled with liquid or not filled with liquid, are separated by the membrane which divides the sterile filter into two chambers.

Generally, a liquid that contains a cleaning and disinfecting agent is located in the substituate segment. The dialysis liquid system of the blood treatment devices is filled with such a liquid after being brought into operation for the first time. This liquid is drained off in the method according to the present invention. Thus, only the rest of the dialysis liquid system remains filled.

A device according to the present invention for carrying out the method according to the present invention makes it possible, after removal of the sterile filter, to easily and safely separate the substituate segment from the rest of the dialysis liquid system and drain off liquid located in the substituate segment. The liquid in the substituate segment can be pumped off, for example. The dialysis liquid pump present in the dialysis liquid system of the known blood treatment device can be started up for this purpose.

The sterile filters used in practice generally have an inlet and an outlet for the first chamber and an inlet and an outlet for the second chamber, so as to be able to operate both chambers in through-flow. If the known sterile filters are used to recover a sterile substituate, dialysis liquid is passed through the first chamber, while the substituate is drawn off from the second chamber. In sterile filters in which the first chamber and second chamber each have an inlet and an outlet, the inlet and outlet of both chambers must be attached to the blood treatment device. Consequently, the blood treatment device has four appliance-side attachment pieces, and the sterile filter has four filter-side attachment pieces. However, it is also possible that the second chamber of the sterile filter used to recover substituate has only an outlet. Then, the blood treatment device only needs to have three appliance-side attachment pieces, and the sterile filter only needs to have three filter-side attachment pieces. The present invention thus provides two alternative embodiments.

In one alternative embodiment, the device according to the present invention has four attachment pieces, wherein the first and second attachment pieces are connected to each other by a first connection line and the third and fourth attachment pieces are connected to each other by a second connection line. With the device according to the present invention, a first flow connection can be established with the two attachment pieces to which the inlet and outlet of one chamber of the sterile filter are attached, and a flow connection can be established with the two attachment pieces to which the inlet and outlet of the second chamber of the sterile filter are attached. In this way, that part of the dialysis liquid system that includes the substituate segment is separated from the rest of the dialysis liquid system. Attachment pieces are understood as all means for establishing a connection or flow connection, and several attachment pieces can also form one unit.

In the other alternative embodiment, the first and second attachment pieces are connected to each other by a first connection line, while the third and fourth attachment pieces are closed in a sterile manner, such that that part of the dialysis liquid system that includes the substituate segment can be separated from the rest of the dialysis liquid system. The third attachment piece can be designed in the manner of a closure cap, which closes the appliance-side attachment piece in a sterile manner when the device according to the present invention is attached to the blood treatment device.

In order to be able to drain off liquid located in the substituate segment, the device according to the present invention has a venting means. The venting means is preferably once again a sterile filter through which air can flow into the volume included by the substituate segment while the liquid is being drained off.

The device according to the present invention can be designed in different ways. The only crucial point is that said flow connections can be established between the appliance-side attachment pieces of the blood treatment device. It is advantageous if the device according to the present invention is designed in the manner of an adapter, which can be connected easily and safely to the appliance-side attachments when the sterile filter is detached from the blood treatment device. The connection lines between the attachment pieces can be fixed or flexible lines. They can be designed as channels in solid bodies or can be hose lines.

The known blood treatment devices have holders for securing the sterile filters. Preferably, the device according to the present invention is designed in such a way that it can be inserted, in place of the sterile filters, with an exact fit into the holders of the blood treatment devices.

The appliance-side attachment pieces and the attachment pieces of the device according to the present invention can be designed as plugs or sockets. Preferably, in each case two attachment pieces of the device according to the present invention form a common plug, which can be inserted with an exact fit into an appliance-side socket of the blood treatment device, to which otherwise the respective attachment pieces of the sterile filter are attached.

BRIEF DESCRIPTION OF THE DRAWINGS

An illustrative embodiment of the present invention is explained in more detail below with reference to the drawings, in which.

DETAILED DESCRIPTION

Figure 1:
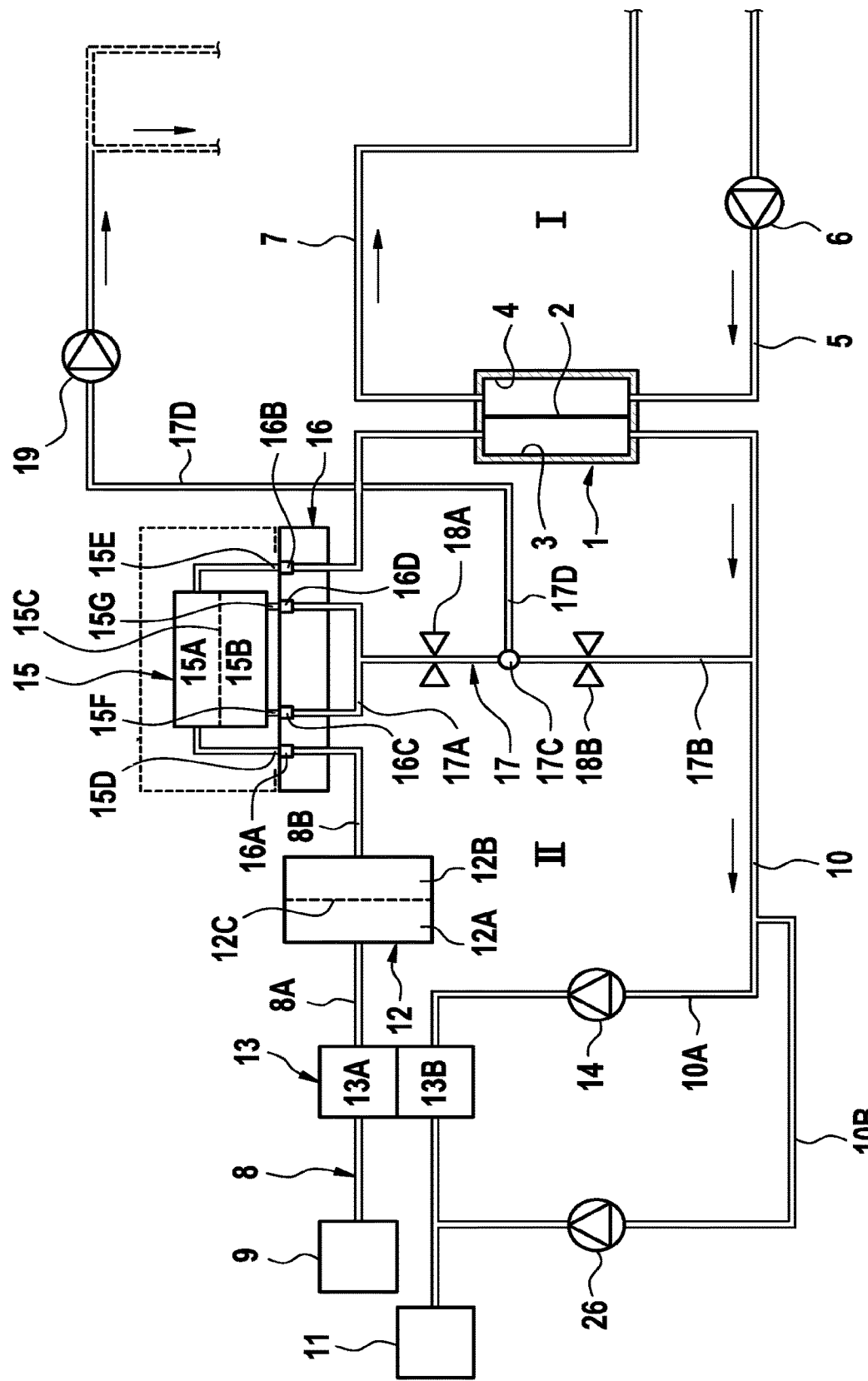
FIG. 1 shows the main components of an extracorporeal blood treatment device, wherein a sterile filter is attached to the blood treatment device for the purpose of recovering a sterile substituate from the dialysis liquid.

The blood treatment device, in particular a hemo(dia) filtration device, has a dialyser 1, which is separated by a membrane 2 into a dialysis liquid chamber 3, through which dialysis liquid flows, and a blood chamber 4, through which blood flows.

A blood delivery line 5, into which a blood pump 6 is coupled, leads to the blood chamber 4, while a blood return line 7 issues from the blood chamber 4. The blood delivery line 5 and blood discharge line 7 form, together with the blood chamber 4, the extracorporeal blood circuit I of the blood treatment device.

The dialysis liquid system II of the blood treatment device is described below. The dialysis liquid system II has a dialysis liquid delivery line 8, which leads from a dialysis liquid source 9 to the dialysis liquid chamber 3, and a dialysis liquid return line 10, which issues from the dialysis liquid chamber 3 and leads to an outlet 11. The dialysis liquid delivery line 8 has a first section 8A, which leads from the dialysis liquid source 9 to the first chamber 12A of a first sterile filter 12. One chamber 13A of a balance device 13 is coupled into the first section 8A of the dialysis liquid delivery line 8. The second section 8B of the dialysis liquid delivery line 8 issues from the second chamber 12B of the first sterile filter 12 and leads to the dialysis liquid chamber 3.

The dialysis liquid return line 10 divides into two sections 10A and 10B, which leads to the outlet 11. A dialysis liquid pump 14 is coupled into the first section 10A, while an ultrafiltrate pump 26 is coupled into the second section 10B. The other chamber 13B of the balance device 13 is also coupled into the first section 10A.

In order to recover a substituate from the dialysis liquid, the hemo(dia)filtration device has a second sterile filter 15, which is divided by a semipermeable membrane 15C into a first chamber 15A and a second chamber 15B. The second sterile filter 15 forms an exchangeable unit, which can be attached to the blood treatment device or removed from the treatment device.

To attach and secure the second sterile filter 15, the blood treatment device has a holder 16, which has a first attachment piece 16A, a second attachment piece 16B, a third attachment piece 16C and a fourth attachment piece 16D. The appliance-side attachment pieces 16A to 16D can be designed as sockets.

The second filter 15 has a first attachment piece 15D, a second attachment piece 15E, a third attachment piece 15F and a fourth attachment piece 15G. The filter-side attachment pieces 15D to 15G can be connected with an exact fit to the appliance-side attachment pieces 16A to 16D. The filter-side attachment pieces can be corresponding plugs.

The third and fourth appliance-side attachment pieces 16C, 16D are connected to each other by a connection line 17A, to which a bypass line 17B is attached. Two shut-off elements 18A and 18B are located on the bypass line 17B. Between the two shut-off elements 18A and 18B, a substituate line 17D, into which a substituate pump 19 is coupled, branches off from a substituate port 17C. The substituate line 17D leads to the extracorporeal blood circuit I upstream or downstream of the blood chamber 4, in order to be able to deliver substituate to the extracorporeal blood circuit I. While the substituate is being delivered, the shut-off element 18A is opened and the shut-off element 18B closed.

The blood treatment device also has further shut-off elements and bypass lines, and other components too, but these are not shown for sake of clarity.

The line sections of the dialysis liquid system II, through which sterile substituate is delivered from the second chamber 15B of the second sterile filter 15 to the extracorporeal blood circuit I, represent the substituate segment 17 that has to be kept free of contaminants, in particular from the formation of a biofilm. The substituate segment therefore comprises all the lines or line sections that include the volume lying downstream of the sterile filter, for example the connection line 17A and the line section of the bypass line 17B upstream of the substituate port 17C.

The blood treatment devices are tested after assembly. The dialysis liquid system II is then filled completely with a liquid that contains a cleaning and disinfecting agent. All the line sections of the dialysis liquid system are thus filled. At this time, the substituate line 17D is not generally attached to the substituate port 17C.

For the subsequent transport and storage of the blood treatment device, the method according to the present invention is carried out using the device according to the present invention.

The first and second sterile filters 12, 15 are removed. The first sterile filter 12 is replaced in a known manner by a known bypass piece. The second sterile filter 15 is replaced by the device according to the present invention, which device is described below with reference to FIG. 2.

The device 20 according to the present invention for carrying out the conservation method has, like the sterile filter 15, a first attachment piece 20A, a second attachment piece 20B, a third attachment piece 20C and a fourth attachment piece 20D, which can be connected to the appliance-side attachment pieces 16A to 16D. The attachment pieces can once again be designed as plugs that can be inserted with an exact fit into sockets.

In a preferred embodiment, the first and third attachment pieces 20A, 20C are designed as a common plug, while the second and fourth attachment pieces 20B, 20D are designed as a second plug. However, all of the attachment pieces can also be separate from one another.

The first and second attachment pieces 20A, 20B are connected to each other by a first connection line 21, and the third and fourth attachment pieces 20C, 20D are connected to each other by a second connection line 22. The first and second connection lines 21, 22 can be hose lines. A third line 23, which is closed by a sterile filter 24, branches off from the second connection line 22. The sterile filter 24 has a first chamber 24A and a second chamber 24B, which are separated by a semipermeable membrane 24C. The first chamber 24A of the sterile filter 24 is connected to the third line 22, in particular a hose line. A hose clamp 25 is provided for clamping off the hose line 23.

The device according to the present invention preferably forms a unit that can be easily and safely secured to the holder 16 in place of the sterile filter 15.

When the device 20 according to the present invention is attached to the blood treatment device, a flow connection is established between the dialysis liquid source 9 and the dialysis liquid chamber 3, while the substituate segment 17 is separated from the rest of the dialysis liquid system. The liquid located in the substituate segment 17 decoupled from the rest of the dialysis liquid system is now drawn off, such that the substituate segment is free of liquid. For this purpose, the shut-off element 25 on the device according to the present invention is opened, such that air can pass into the substituate segment in order to vent the volume enclosed by the substituate segment 17. The liquid can be conveyed, for example, to the outflow 11, for which purpose the pumps 14 and 26 can be operated. The shut-off element 25 is then closed again, and the rest of the dialysis liquid system is filled completely with a liquid that contains an antifreeze agent. The blood treatment device remains in this state until installation at the dialysis centre.

When the dialysis device is started up, new sterile filters 12 and 15 are used. The compulsory cleaning and disinfecting cycle then follows. Any bacteria are either killed off or flushed out by the direct cleaning and disinfecting. Thus, the first use of a filter and all subsequent exchanges can be classed as aseptic procedures, which guarantee that the substituate segment is permanently sterile.

It has been found in tests that, in the substituate segment not filled with antifreeze agent, and even after quite a long storage period, a biofilm cannot form that cannot be safely and quickly removed using conventional cleaning and disinfecting measures.

Figure 2:
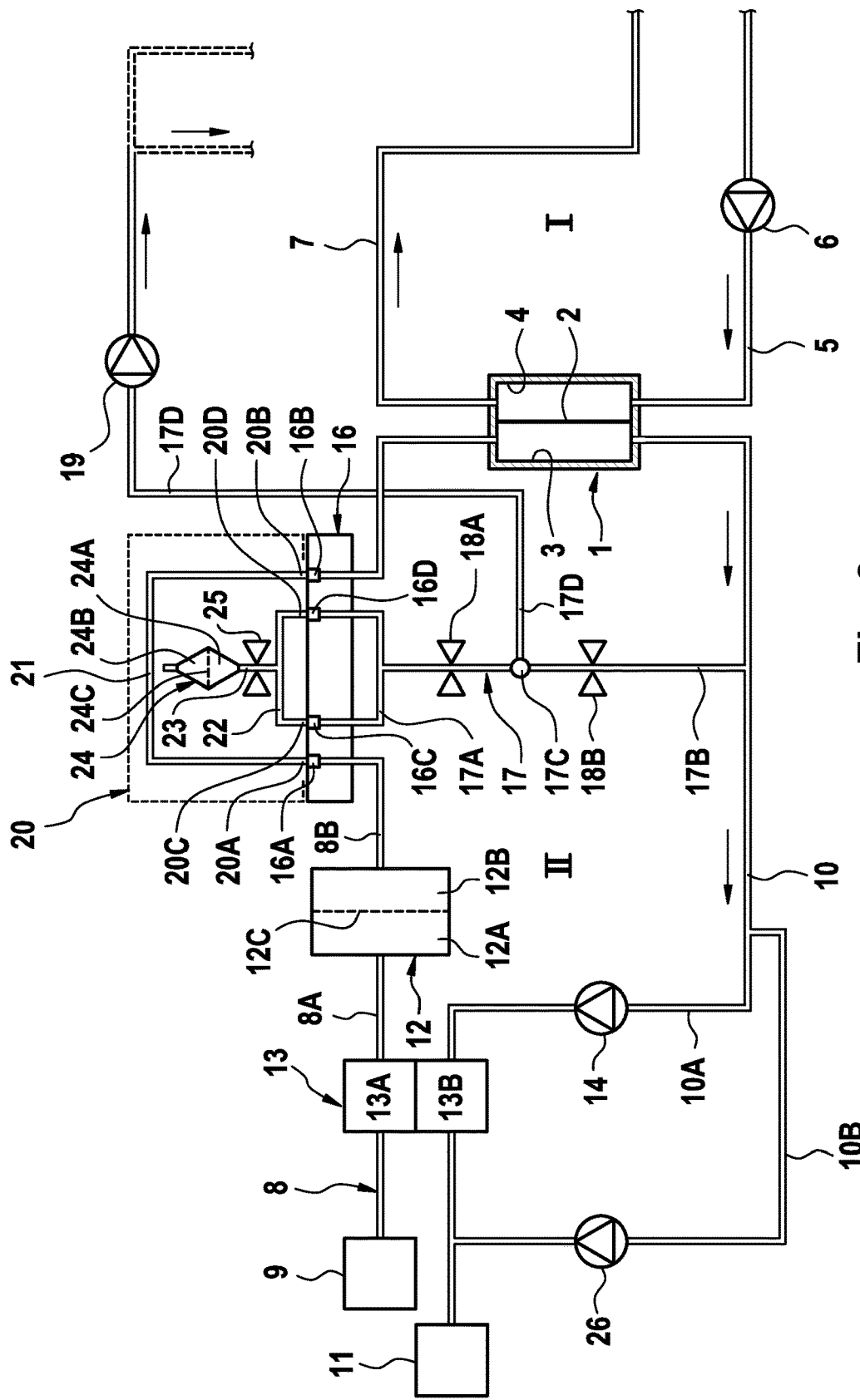
FIG. 2 shows the extracorporeal blood treatment device from FIG. 1, wherein the device according to the present invention is attached to the blood treatment device for the purpose of carrying out a method for conserving the blood treatment device.
Figure 3:
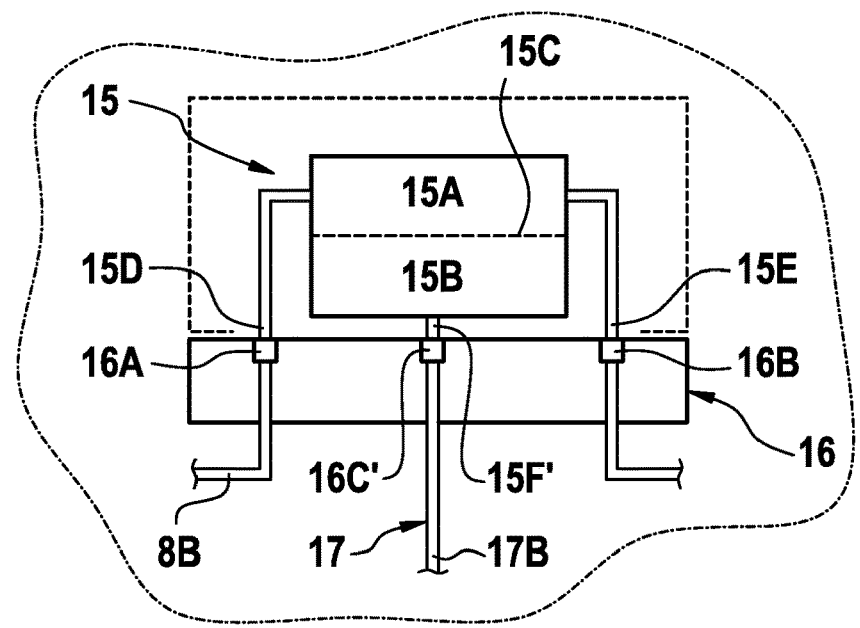
FIG. 3 shows a partial view of an alternative embodiment of the blood treatment device from FIG. 1, wherein an alternative embodiment of the sterile filter is attached to the blood treatment device for the purpose of recovering a sterile substituate from the dialysis liquid.
Figure 4:
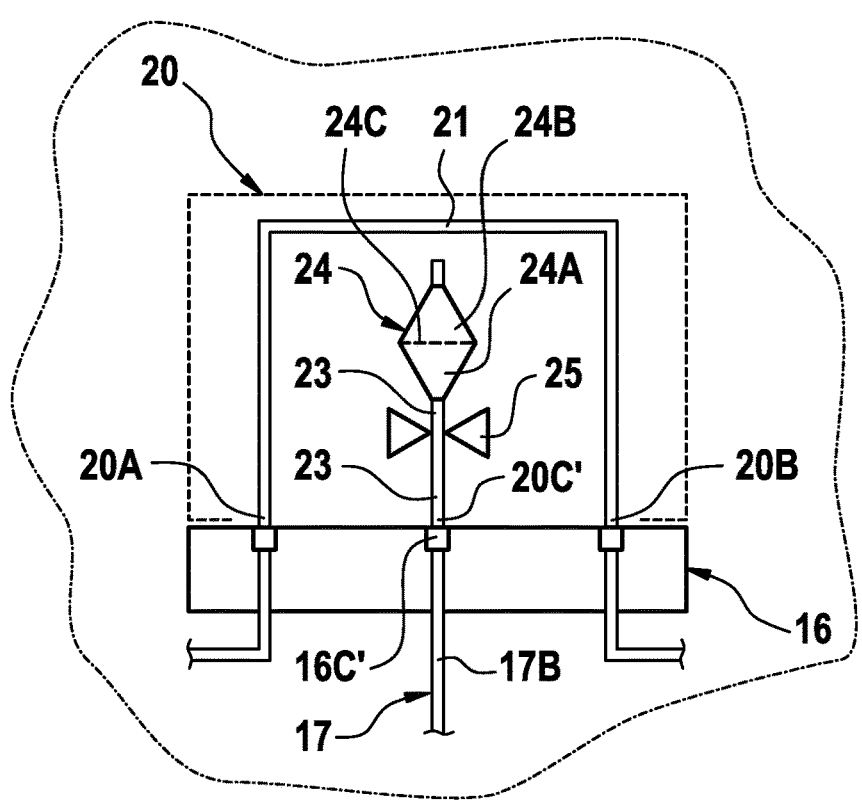
FIG. 4 shows the blood treatment device from FIG. 3, wherein an alternative embodiment of the device according to the present invention is attached to the blood treatment device for the purpose of recovering a sterile substituate from the dialysis liquid.

An alternative embodiment of the blood treatment device, and of the device according to the present invention for attachment to the blood treatment device, is described below with reference to FIGS. 3 and 4, which embodiment differs from the embodiment described with reference to FIGS. 1 and 2 only in that the blood treatment device and the device according to the present invention have only three attachment pieces. The corresponding parts are provided in FIGS. 3 and 4 with the same reference signs as in FIGS. 1 and 2. Instead of the two filter-side attachment pieces 15F and 15G (FIG. 1), the second chamber 15B of the second sterile filter 15 has only one attachment piece 15F' (FIG. 3), and, instead of the two appliance-side attachment pieces 16C and 16D (FIG. 1), the blood treatment device has only one attachment piece 16C' (FIG. 3), wherein the third filter-side attachment piece 15F' is attached to the third appliance-side attachment piece 16C' (FIG. 3). A connection line for the connection of two appliance-side attachment pieces is not required here. The bypass line 17B of the substituate segment 17 is therefore connected directly to the third appliance-side attachment piece 16C'. The first chamber 24A of the sterile filter 24 is connected directly to the third attachment piece 20C' of the device 20 according to the present invention via the connection line 23 (FIG. 4), such that the substituate segment 17 is closed in a sterile manner (FIG. 4) when the device according to the present invention is attached to the blood treatment device.

What is claimed is:

1. A system comprising an extracorporeal blood treatment device, a sterile filter in the form of an exchangeable unit configured to be attached to and removed from the extracorporeal blood treatment device, and a conserving device for conserving the extracorporeal blood treatment device and configured to replace the sterile filter and to be attached to and removed from the extracorporeal blood treatment device, the extracorporeal blood treatment device comprising a dialysis liquid system and a substituate segment, the dialysis liquid system comprising a dialysis liquid delivery line and a dialysis liquid return line, the extracorporeal blood treatment device being configured to receive, exchangeably, the sterile filter and the conserving device, wherein the extracorporeal blood treatment device comprises a dialysis fluid line first socket, an end of a first dialysis fluid line that terminates at the dialysis fluid line first socket, a dialysis fluid line second socket, an end of a second dialysis fluid line that terminates at the dialysis fluid line second socket, a substituate line third socket, an end of a substituate line that terminates at the substituate line third socket, and a holder comprising the dialysis fluid line first socket, the dialysis fluid line second socket, and the substituate line third socket, the sterile filter comprises a first attachment piece, a two-chamber filter, a first line connecting the first attachment piece to a first chamber of the two-chamber filter, a second attachment piece, a second line connecting the second attachment piece to the first chamber of the two chamber filter, a third attachment piece, and a third line connecting a second chamber of the two chamber filter to the third attachment piece, wherein the first, second, and third attachment pieces are arranged to enable an exact fit to the first, second, and third sockets, respectively, and the conserving device comprises:

a first attachment plug configured to attach in a plug-socket arrangement to the dialysis fluid line first socket;

a second attachment plug configured to attach in a plug-socket arrangement to the dialysis fluid line second socket;

a third attachment plug configured to attach in a plug-socket arrangement to the substituate line third socket;

a first connection line connecting the first attachment plug and the second attachment plug to each other; and a venting device comprising a second sterile filter, a valve, and a second connection line, the second sterile filter and the valve being connected to the third attachment plug through the second connection line, the venting device being configured to allow air to flow into the substituate segment to vent a volume enclosed by the substituate segment, wherein the second connection line is separate from and not connected to the first connection line such that, when the conserving device is attached to the extracorporeal blood treatment device, the substituate segment is separated from the dialysis liquid delivery line.

2. A system comprising an extracorporeal blood treatment device, a sterile filter in the form of an exchangeable unit configured to be attached to and removed from the extracorporeal blood treatment device, and a conserving device for conserving the extracorporeal blood treatment device and configured to replace the sterile filter and to be attached to and removed from the extracorporeal blood treatment device, the extracorporeal blood treatment device comprising a dialysis liquid system and a substituate segment, the dialysis liquid system comprising a dialysis liquid delivery line and a dialysis liquid return line, the extracorporeal blood treatment device being configured to receive, exchangeably, the sterile filter and the conserving device, wherein the extracorporeal blood treatment device comprises a dialysis fluid line first socket, an end of a first dialysis fluid line that terminates at the dialysis fluid line first socket, a dialysis fluid line second socket, an end of a second dialysis fluid line that terminates at the dialysis fluid line second socket, a substituate line third socket, an end of a first substituate line that terminates at the substituate line third socket, a substituate line fourth socket, an end of a second substituate line that terminates at the substituate line fourth socket, and a holder comprising the dialysis fluid line first socket, the dialysis fluid line second socket, the substituate line third socket, and the substituate line fourth socket, the sterile filter comprises a first attachment piece, a two-chamber filter, a first line connecting the first attachment piece to a first chamber of the two-chamber filter, a second attachment piece, a second line connecting the second attachment piece to the first chamber of the two-chamber filter a third attachment piece, a third line connecting a second chamber of the two-chamber filter to the third attachment piece, a fourth attachment piece and a fourth line connecting the second chamber of the two-chamber filter to the fourth attachment piece, wherein the first, second, third, and fourth attachment pieces are arranged to enable an exact fit to the first, second, third, and fourth sockets, respectively, and the conserving device comprises:

a first attachment plug configured to attach in a plug-socket arrangement to the dialysis fluid line first socket;

a second attachment plug configured to attach in a plug-socket arrangement to the dialysis fluid line second socket;

a third attachment plug configured to attach in a plug-socket arrangement to the substituate line third socket;

a fourth attachment plug configured to attach in a plug socket arrangement to the substituate line fourth socket;

a first connection line connecting the first attachment plug and the second attachment plug to each other; and a venting device comprising a second sterile filter, a valve, and a second connection line, the second sterile filter and the valve being connected to the third and fourth attachment plugs through the second connection line, the venting device being configured to allow air to flow into the substituate segment to vent a volume enclosed by the substituate segment, wherein the second connection line is separate from and not connected to the first connection line such that, when the conserving device is attached to the extracorporeal blood treatment device, the substituate segment is separated from the dialysis liquid delivery line.

3. The system according to claim 1, wherein the second sterile filter is divided by a membrane into a third chamber and a fourth chamber, and the third chamber is connected to the third attachment plug.

4. The system according to claim 3, wherein the third chamber is connected to the third attachment plug by the second connection line.

5. The system according to claim 2, wherein the second sterile filter is divided by a membrane into a third chamber and a fourth chamber, and the third chamber is connected to the second connection line connecting the third and fourth attachment plugs.

6. The system according to claim 5, wherein the third chamber is connected to the second connection line connecting the third and fourth attachment plugs via a third connection line on which the valve is provided.

7. The system according to claim 1, wherein the first and third attachment plugs are designed as a common first plug, or the second and third attachment plugs are designed as a common second plug.

8. The system according to claim 2, wherein the first and third attachment plugs are designed as a common first plug, and the second and fourth attachment plugs are designed as a common second plug.

9. The system of claim 1, wherein the first connection line comprises a channel in a solid body.

10. The system of claim 1, wherein the first connection line comprises a hose line.

11. The system of claim 1, wherein the valve is arranged between the second sterile filter and the third attachment plug, and is closed.

12. The system of claim 1, wherein the sterile filter is removed from the extracorporeal blood treatment device and the conserving device is attached to the extracorporeal blood treatment device.

13. The system of claim 1, wherein the conserving device is removed from the extracorporeal blood treatment device and the sterile filter is attached to the extracorporeal blood treatment device.

14. The system of claim 2, wherein the first connection line comprises a channel in a solid body.

15. The system of claim 2, wherein the first connection line comprises a hose line.

16. The system of claim 2, wherein the valve is arranged between the second sterile filter and the third attachment plug, between the second sterile filter and the fourth attachment plug, and is closed.

17. The system of claim 2, wherein the sterile filter is removed from the extracorporeal blood treatment device and the conserving device is attached to the extracorporeal blood treatment device.

18. The system of claim 2, wherein the conserving device is removed from the extracorporeal blood treatment device and the sterile filter is attached to the extracorporeal blood treatment device.

* * * * *